(12) United States Patent
Yi et al.

(10) Patent No.: US 9,611,217 B2
(45) Date of Patent: Apr. 4, 2017

(54) SYNTHETIC PROCESSES OF CARPROFEN

(71) Applicants: Lin Yi, Milford, CT (US); Xiping Su, Woodbridge, CT (US); Peter Werth, Woodbridge, CT (US)

(72) Inventors: Lin Yi, Milford, CT (US); Xiping Su, Woodbridge, CT (US); Peter Werth, Woodbridge, CT (US)

(73) Assignee: ChemWerth, Inc., Woodbridge, CT (US)

( * ) Notice: Subject to any disclaimer, the term of this patent is extended or adjusted under 35 U.S.C. 154(b) by 0 days.

(21) Appl. No.: 15/147,671

(22) Filed: May 5, 2016

(65) Prior Publication Data

US 2016/0326113 A1    Nov. 10, 2016

Related U.S. Application Data

(60) Provisional application No. 62/157,820, filed on May 6, 2015.

(51) Int. Cl.
| | | |
|---|---|---|
| *C07D 209/88* | (2006.01) | |
| *C07D 207/20* | (2006.01) | |
| *C07C 243/22* | (2006.01) | |
| *C07D 295/135* | (2006.01) | |

(52) U.S. Cl.
CPC .......... *C07D 209/88* (2013.01); *C07C 243/22* (2013.01); *C07D 295/135* (2013.01)

(58) Field of Classification Search
CPC ... C07D 209/88; C07D 207/20; A61K 31/403
USPC .................................. 548/444, 439; 514/411
See application file for complete search history.

(56) References Cited

U.S. PATENT DOCUMENTS

| | | |
|---|---|---|
| 3,896,145 A | 7/1975 | Berger et al. |
| 4,057,640 A | 11/1977 | Biere et al. |
| 4,150,031 A | 4/1979 | Berger et al. |
| 4,158,007 A | 6/1979 | Gurien et al. |
| 4,264,500 A | 4/1981 | Zwahlen |

FOREIGN PATENT DOCUMENTS

| | | |
|---|---|---|
| CN | 101492412 A | 7/2009 |
| CN | 101492413 A | 7/2009 |
| EP | 0151423 A2 | 8/1985 |
| EP | 0247222 A1 | 12/1987 |
| WO | 8700519 A1 | 1/1987 |

OTHER PUBLICATIONS

European Examination Report of EP Application No. 16168594.6. Applicant: Chemwerth, Inc. Title: Synthetic process of carprofen. 39 pages. Jun. 22, 2016.
European Search Report and Examination European Patent Application No. 16168594 Date: Jun. 22, 2016 3 pages.
Jun Chen and Zhen-hua Zhou; "Synthesis of Animal Drug Carprofen", Shangdong Chemical Industry; vol. 34, No. 4 (2005); pp. 5-6.
Liu, et al., "Synthesis of Carprofen", Zhejiang Huagong, vol. 43, No. 8 (2012); pp. 21-23.
Percy S. Manchand, David L. Coffen, et al; "Synthesis of Carprofen, a Carbazole-based Non-teroidal Anti-inflammatroy Agent"; Hetrocycles; vol. 39, No. 2 (1994), pp. 833-845.
Anderson, et al., "553. The preparation of dimethyltetrahydrocarbazoles", Journal of the Chemical Society, Jan. 1, 1950, pp. 2855-2857.
Emile Bisagni, et al., "Aromatisation des Dihydro-3,4 C<arbazole(2H)ONES-I par le chlorure de pyridinium", Tetrahedron, vol. 36, No. 10, Jan. 1, 1980 (Jan. 1, 1980). pp. 1327-1330.
Carlsson, et al., "Enamine Chemistry XX. Synthesis of Furan Derivatives by Reductive Cyclisation of Enamines", Bulletin Des Societes Chimiques Belges, vol. 89, No. 8, Jan. 1, 1980, pp. 643-650.
Wenkert, et al., "Synthesis of Olivacine", Journal of the American Chemical Society, vol. 84, No. 1, Jan. 1, 1962, pp. 94-97.

*Primary Examiner* — Alicia L Otton
*Assistant Examiner* — Sagar Patel
(74) *Attorney, Agent, or Firm* — St. Onge Steward Johnston & Reens, LLC (57) ABSTRACT

Methods and intermediates for the synthesis of carprofen and its derivatives starting from cyclohexanone are disclosed.

8 Claims, 3 Drawing Sheets

SYNTHETIC PROCESSES OF CARPROFEN

FIELD OF THE INVENTION

The present invention relates to processes of manufacturing carprofen and its derivatives.

BACKGROUND OF THE INVENTION

Carprofen is a non-steroidal anti-inflammatory drug (NSAID) of the propionic acid class that includes ibuprofen, naproxen, and ketoprofen. Carprofen reduces inflammation by inhibition of COX-2 and other sources of inflammatory biological targets. Carprofen has been approved by FDA as a veterinary drug for the relief of pain and inflammation associated with osteoarthritis and for the control of postoperative pain associated with soft tissue and orthopedic surgeries for dogs. Carprofen is supplied under the trade names Rimadyl, Novox, and Vetprofen in the dosages of 25 mg, 75 mg, and 100 mg of carprofen per tablet or caplet.

Carprofen is a white, crystalline compound. Carprofen is freely soluble in ethanol, but practically insoluble in water at 25° C. Carprofen is the nonproprietary designation for a substituted carbazole, 6-chloro-α-methyl-9H-carbazole-2-acetic acid. The empirical formula is $C_{15}H_{12}ClNO_2$ and the molecular weight 273.72. The chemical structure of carprofen is:

The synthesis of carprofen was first reported in 1970s by a group of scientists at Hoffmann-La Roche Inc. in U.S. Pat. No. 4,158,007. According to the patent, carprofen can be prepared by using cyclohexenone and 2-methylmalonate as starting materials, as summarized below:

The starting material, cyclohexenone, is expensive. As a reference point, Sigma-Aldrich sells it at $120.50 per 0.1 liter. Consequently, the above process is not suitable for the manufacture of carprofen on an industrial scale.

Scientists at Hoffmann-La Roche Inc. later reported what they thought a better process to prepare carprofen in EP 0,151,423 by starting from carbazole, as summarized below:

Carprofen

Carprofen

However, the process is also not suitable for industrial manufacturing because it requires the use of toxic trimethylsilyl cyanide as a reagent and it forms isomers during the chlorination step and the subsequent step. Additionally, carbazole is an expensive starting material, currently sold at a price of $111.50 per 0.2 gram at Sigma-Aldrich.

Thereafter, scientists at Hoffmann-La Roche reported a different, improved chemical process to make carprofen and its derivatives, again starting from carbazole, in EP 0,247,222.

The above chemical process eliminates the need to use toxic trimethylsilyl cyanide. The chemical process was further optimized by a group of Chinese scientists, as reported in CN 101492412. Nevertheless, the chemical process is still not ideal because the chlorination step therein is too complicated because it requires region-selective chlorination at two specific sites of the molecule.

A few other synthetic routes to prepare carprofen were reported in U.S. Pat. Nos. 4,150,031 and 4,264,500. Again, they use carbazole or a derivative thereof as a starting material. For example, U.S. Pat. No. 4,150,031 discloses that:

Carprofen

The lengthy synthetic steps and stringent reaction conditions of the above process make it unsuitable for a large scale production.

WO 87/00519 discloses a process of making carprofen starting from 7-chloro-3-bromocarbazole via a coupling reaction and an oxidation reaction as shown below:

This process is not practical for industrial manufacturing of carprofen because the starting material, 7-chloro-3-bromocarbazole, itself requires multiple-step synthesis.

Therefore, there is a need in the industry to provide an economical, efficient and viable process for the preparation of carprofen that is suitable for industrial scale manufacturing.

SUMMARY OF THE INVENTION

In one aspects, the present invention provides novel processes for preparing carprofen and derivatives that are environmental friendly, economical, and industrially feasible.

According to one embodiment, carprofen and its analogs may be prepared by:

(1) heating cyclohexanone and a first base, with or without an acidic catalyst, in a first organic solvent to form an enamine; wherein the first base is an organic secondary base, which may be, but not limited to, pyrrolidine or piperidine; wherein the acidic catalyst may include, but not limited to, toluene sulfonic acid, molecular sieves, and macroporous sulfonic acid resin;

(2) reacting the enamine with an α-substituted carboxylic acid ester in a second organic solvent to afford a 2-substituted cyclohexanone;

(3) reacting the 2-substituted cyclohexanone with a formic acid ester in the presence of a second base to form 2,2'-disubstituted cyclohexanone; wherein the second base may be, but is not limited to, sodium methoxide;

(4) reacting the 2,2'-disubstituted cyclohexanone in a third organic solvent with an aqueous solution of a substituted phenyldiazonium salt to give a substituted hydrazine compound, wherein one nitrogen of the hydrazine compound is attached to a substituted phenyl group and the other nitrogen of the hydrazine compound is attached to the cyclohexanone ring, forming a conjugation of "—N═C—C(O)—", wherein the substituted phenyldiazonium salt may be, but is not limited to hydrochloric salt thereof; and (5) subjecting the substituted hydrazine compound to Fisher indole conditions to form a tricyclic compound followed by aromatization of the non-indole cyclic ring to form carprofen or its derivatives. An acidic catalyst, such as hydrochloric acid or sulfuric acid, may be used in the ring closure and aromatization reactions.

According to another embodiment, carprofen and its analogs may be prepared by:

(1) forming an enamine from cyclohexanone by following the first step of the previous embodiment;

(2) reacting the enamine with an α-substituted carboxylic acid ester, optionally with a catalyst, in an organic solvent, followed by treatment with a base to afford a 2-substituted cyclohexanone enamine; wherein the catalyst may be, but is not limited to, sodium iodide; and wherein the base may be, but is not limited to DIEA (diisopropylethylamine), DBU (1,8-diazabicyclo[5.4.0]undec-7-ene), sodium hydride, sodium alkoxide, potassium carbonate, or cesium carbonate.

(3) reacting the 2-substituted cyclohexanone enamine in an organic solvent with an aqueous solution of a substituted phenyldiazonium salt to give a substituted hydrazone salt, wherein one nitrogen of the hydrazone salt is attached to a substituted phenyl group and the other nitrogen of the hydrazone salt is attached to the cyclohexanone enamine ring, forming a conjugation of "—N═C—C(O)—"; wherein the substituted phenyldiazonium salt may be, but is not limited to a tetrafluorboric salt, and (4) subjecting the substituted hydrazone salt to Fisher indole conditions to form a tricyclic compound followed by aromatization of the non-indole cyclic ring so that the tricyclic rings are all aromatized and conjugated. An acidic catalyst may be used in the Fisher indole reaction. Suitable acidic catalysts include, but are not limited to, polyphosphoric acid, 7.7 wt. % phosphorus pentoxide in methanesulfonic acid, and concentrated sulfuric acid in dioxane. The aromatization reaction may be carried out by adding an organic salt and heating the resulting mixture at a temperature of 200-200° C. The organic salt may be, but is not limited to, pyridine hydrochloride. During the aromatization reaction, the enamine functional group is simultaneously removed which eventually leads to carprofen or its derivatives.

One advantage of the processes is that the starting material, cyclohexanone, is cheap and readily available.

Another advantage of the processes is that purification of many intermediates formed during the processes can be avoided. In other words, the intermediates can be used directly in the subsequent reactions without purification. As such, the processes are efficient.

A further advantage is that the processes are safe and environmentally friendly. There are no hazardous byproducts produced by the processes.

The processes of the present invention are amenable for preparing analogs (i.e., derivatives) of carprofen.

In another aspect, the present invention provides novel chemicals and intermediates prepared by the above mentioned processes.

DESCRIPTION OF THE INVENTION

In one aspect, the present invention provides novel processes for preparing carprofen starting from cyclohexanone or its derivatives.

Figure 1:
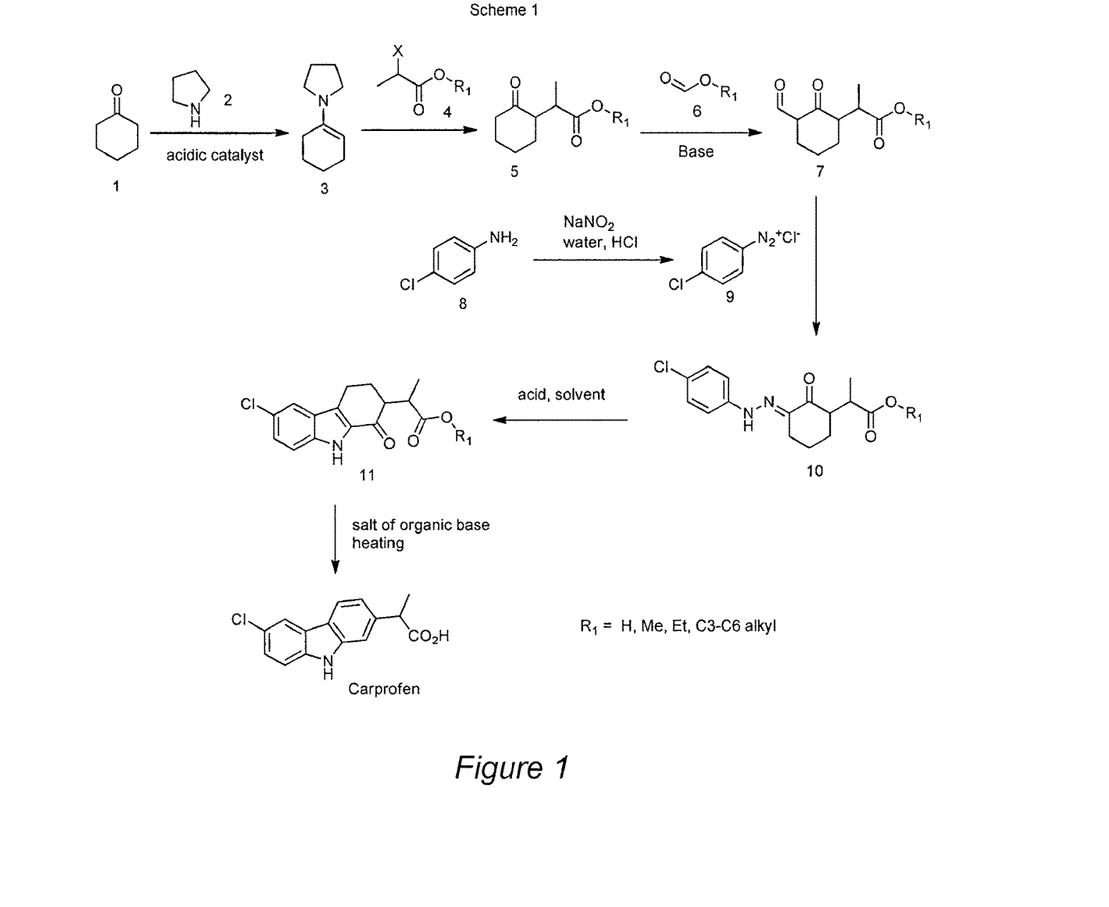
FIG. 1 shows one synthetic scheme to prepare carprofen according to one embodiment of the invention.

According to FIG. 1 (Scheme 1), the synthetic process starts with synthesis of an enamine of formula 3 by heating to reflux a mixture of cyclohexanone of formula 1 or its derivatives or other cyclic ketones with 0.5-2 equivalent ("equiv.") of pyrrolidine of formula 2 or piperidine or other cyclic or acyclic organic secondary base in an organic solvent, such as toluene, cyclohexane and benzene, with or without an acidic catalyst, such as toluene sulfonic acid, molecular sieves, and macroporous sulfonic acid resin. As an example, FIG. 1 shows that the enamine of formula 3 is prepared by using piperidine as a secondary base, toluene as a solvent, and molecular sieves as catalysts.

The enamine of formula 3 is then treated with an α-substituted carboxylic acid ester of formula 4 (more specifically, an α-substituted propanoic acid ester) under heating in an organic solvent, such as methanol or acetonitrile, to afford a 2-substituted cyclohexanone of formula 5. $R_1$ may be chosen from the group consisting of hydrogen, methyl, ethyl, and $C_3$-$C_6$ alkyl group; and X may be chloride or bromide.

The 2-substituted cyclohexanone of formula 5 is then converted to a compound of formula 7 by reacting with a base, such as sodium methoxide, in the presence of a formic acid ester of formula 6 at a low temperature. A solution of the compound of formula 7 in an organic solvent, such as methanol, is treated with an aqueous solution of a diazonium of formula 9 to give a compound of formula 10. The diazonium of formula 9 is prepared from an aniline analog of formula 8 (e.g., aniline, 4-chloroaninline, 4-bromoaniline, or 3-chloroaniline) by reacting the aniline analog of formula 8 with sodium nitrite in hydrochloric acid and water. A preferred aniline is 4-chloroaninline, as shown in FIG. 1. Preferably, the substituted phenyldiazonium salt is freshly made and used immediately. Though the diazonium of formula 9 is shown as a hydrochloric salt, the process is not limited to hydrochloric salt, other substituted phenyldiazonium salt may be used. Thus, suitable diazoniums may be shown as formula 9', wherein Y may be any type of typical anions, including chloride and tetrfluoroboric anions:

9'

The compound of formula 10 is then converted to a compound of formula 11 under Fisher indole synthesis conditions by heating a mixture of the compound of formula 10 in an organic solvent, such as acetonitrile, acetic acid, methanol, or dioxane, with or without an acidic catalyst, such as hydrochloric acid or sulfuric acid. Heating a mixture of the compound of formula 11 with a salt of an organic salt, such as pyridine hydrochloride, provides carprofen in good yields.

A person skilled in the art would understand that other similar starting materials and reagents may be used to carry out the process of Scheme 1 under the same conditions, which leads to different intermediates having the same core skeleton (e.g., compounds of formulae 10' and 11'). For example, in lieu of cyclohexanone 1, other ketone may be used (which may result in different "n" in the compounds of formulae 10' and 11'); in lieu of α-substituted propanoic acid methyl ester of formula 4, a different ester of a different carboxylic acid may be used (which may result in different $R_1$, $R_3$ in the compounds of formulae 10' and 11'); and in lieu of the aniline formula of 8, any aniline compound with a different substitution group on the phenyl ring may be used (which may result in different $R_2$ in the compounds of formulae 10' and 11'). Thus, the process is suitable for preparing the compound of formula 10' and the compound of formula 11':

10'

$R_1$ = H, Me, Et, C3-C6 alkyl
$R_2$ = H, 4-Cl, 3-Cl, 2-Cl, 4-Br, 4-F, 3, 4-Di-Cl$_2$
$R_3$ = H, Me, Et, C3-C6 alkyl
n = 0, 1, 2, 3

11'

$R_1$ = H, Me, Et, C3-C6 alkyl
$R_2$ = H, 4-Cl, 3-Cl, 2-Cl, 4-Br, 4-F, 3, 4-Di-Cl$_2$
$R_3$ = H, Me, Et, C3-C6 alkyl
N = 0, 1, 2, 3

Figure 2:
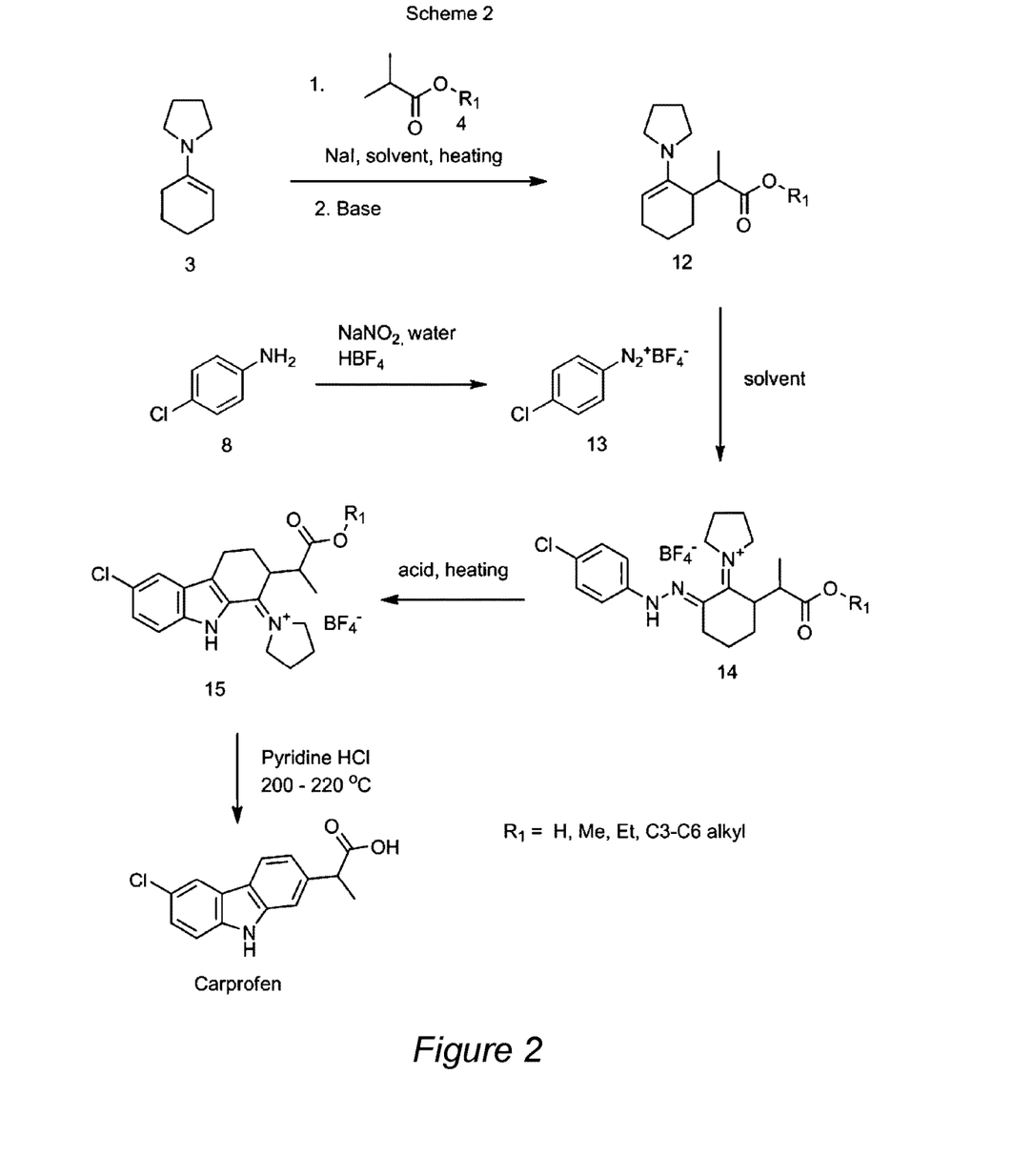
FIG. 2 shows another synthetic scheme to prepare carprofen according to another embodiment of the invention.

According to FIG. 2 (Scheme 2), an enamine of formula 3 reacts with an α-substituted carboxylic acid (propanoic acid) ester of formula 4 under heating in an organic solvent, such as methanol, toluene, dioxane, THF, or acetonitrile, with or without a catalyst, such as sodium iodide, followed by direct treatment with a base such as DIEA, DBU, sodium hydride, sodium alkoxide, potassium carbonate, or cesium carbonate to afford an enamine of formula 12. The enamine of formula 3 may be prepared from refluxing a mixture of cyclohexanone of formula 1 and pyrrolidine of formula 2 as described in Scheme 1. As an example, FIG. 2 shows that the enamine of formula 12 is prepared by acetonitrile as a solvent and sodium iodide as a catalyst.

The enamine of formula 12 is then treated with a diazonium salt of formula 13 in an organic solvent, such as THF (tetrahydrofuran) or acetonitrile, at a low temperature to afford a compound of formula 14. The diazonium salt of formula 13 is prepared from an aniline of formula 8 or one of its analogs (e.g., aniline, 4-chloroaninline, 4-bromoaniline, 3-chloroaniline) by treating it with sodium nitrite, HBF$_4$ (tetrafluoroboric acid) in an acidic aqueous medium at ambient temperature. It is discovered that the tetrafluoroboric acid salt of the diazonium compound is stable. Though the diazonium of formula 14 is shown as a tetrafluoroboric acid salt, the process is not limited to producing the tetrafluoroboric acid salt. Other diazonium phenyldiazonium salt, such as a compound of formula 14" may be produced from using as a compound of formula 9', wherein Y may be any type of typical anions, including chloride and tetrfluoroboric anions:

R$_1$ = H, Me, Et, C$_3$-C$_6$ alkyl

The compound of formula 14 is then converted to a tricyclic compound of formula 15 under Fisher indole conditions by heating it in an anhydrous and acidic environment, such as PPA (polyphosphoric acid), Eaton's reagent (7.7 wt. % phosphorus pentoxide in methanesulfonic acid), concentrated sulfuric acid in dioxane. Alternatively, the compound of formula 11 may be formed from the compound of formula 14 under Fisher indole conditions (not shown in the figures). It is noticed that anhydrous non-protic and acidic solvent and reagent conditions is more likely to convert the compound of formula 14 to the compound of formula 15; an aqueous acidic solvent system, such as hydrochloric acid, is more likely to convert the compound of formula 14 to the compound of formula 11. Other acidic protic solvent system, such as anhydrous acetic acid, give a mixture of compounds of formulae 11 and 15. Though the compound of formula 15 is shown as a tetrafluoroboric acid salt, the process is not limited to producing the tetrafluoroboric acid salt of the tricyclic compound. Depending the compounds of formulae 9' and 14" used, other salts of the tricyclic compound may be produced. Thus, suitable salts of the tricyclic compound may be shown as formula 15", wherein Y may be any type of typical anions, including chloride and tetrfluoroboric anions:

R$_1$ = H, Me, Et, C3-C6 alkyl

The compound of formula 11 and/or 15 is then converted to carprofen by heating it with a salt of an organic salt, such as pyridine hydrochloride, for example, at 200-220° C.

A person skilled in the art would understand that other similar starting materials and reagents can be used to carry out the process of Scheme 2 under the same conditions, which leads to different intermediates having the same core skeleton (e.g., compounds of formulae 14' and 15'). For example, in lieu of enamine of cyclohexanone 3, other enamine may be used (which may result in different "n" in the compounds of formulae 14' and 15'); in lieu of α-substituted propanoic acid methyl ester of formula 4, a different ester of a different carboxylic acid may be used (which may result in different R$_1$, R$_3$ in the compounds of formulae 14' and 15'); and in lieu of the aniline formula of 8, any aniline compound with a different substitution group on the phenyl ring may be used (which may result in different R$_2$ in the compounds of formulae 14' and 15'). Thus, the process is suitable for preparing the compounds of formula 14' and formula 15':

14'

R$_1$ = H, Me, Et, C3-C6 alkyl
R$_2$ = H, 4-Cl, 3-Cl, 2-Cl, 4-Br, 4-F, 3,4-Di-Cl$_2$
R$_3$ = H, Me, Et, C3-C6 alkyl
N = 0, 1, 2, 3

15'

R$_1$ = H, Me, Et, C3-C6 alkyl
R$_2$ = H, 4-Cl, 3-Cl, 2-Cl, 4-Br, 4-F, 3,4-Di-Cl$_2$
R$_3$ = H, Me, Et, C3-C6 alkyl
N = 0, 1, 2, 3

Figure 3:
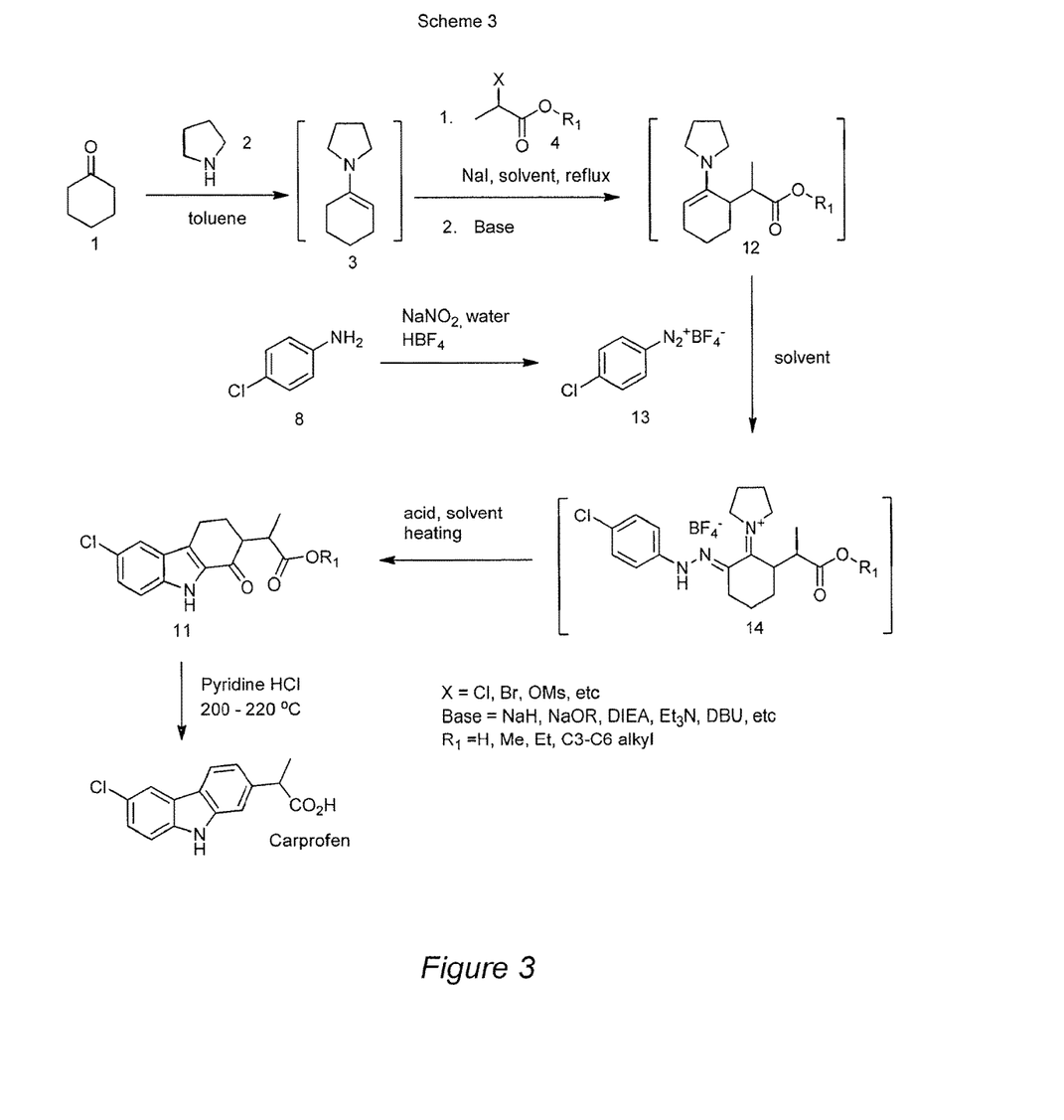
FIG. 3 shows yet another synthetic scheme to prepare carprofen according to a further embodiment of the invention.

FIG. 3 (Scheme 3) represents yet another, more simplified, chemical process for the synthesis of carprofen. A main difference between Scheme 3 and Scheme 2 is that several intermediates of Scheme 3 are not isolated and/or purified during the process; rather, the crude intermediates are directly used in the subsequent reactions. As a result, it is very similar to "one pot" reaction. It is much easier and more efficient to carry out the process of Scheme 3. In Scheme 3, squared brackets are used to indicate that a formula contained therein is not isolated and/or purified before it is used in the next reaction step.

The process begins with a reaction of cyclohexanone 1 or its derivatives or other cyclic ketones with 0.5-2 equiv. of pyrrolidine 2 or piperidine or other cyclic or acyclic organic secondary amines in an organic solvent, such as toluene, cyclohexane, or benzene, with or without an acidic catalyst. The acidic catalyst may be toluene sulfonic acid, molecular sieves, or macroporous sulfonic acid resin. As an example, FIG. 3 shows that the enamine of formula 3 is prepared by using piperidine as a secondary base and toluene as a solvent. After the reaction is complete, simple filtration and evaporation of the reaction mixture afford a crude enamine of formula 3, which can be directly used in the next reaction step without further purification.

Without further purification, the crude enamine of formula 3 is treated with an α-substituted carboxylic acid ester of formula 4 under heating in an organic solvent, such as methanol or acetonitrile, with or without a catalyst, such as sodium iodide, followed by direct treatment with a base, such as DIEA, DBU, sodium hydride, sodium alkoxide, potassium carbonate, or cesium carbonate, followed by simple evaporation to give a crude enamine of formula 12.

Without further purification, the crude enamine of formula 12 is then directly converted to a compound of formula 14 by reacting with a boron tetrafluoride salt of a diazonium salt of formula 13 at a low temperature in an anhydrous solvent, such as acetonitrile or THF. The diazonium salt of formula 13 is prepared from an aniline of formula 8 or its analogs, as described in Scheme 2. A crude compound of formula 14 is obtained by simple organic solvent extraction, aqueous washing, and evaporation.

Without further purification, the crude compound of formula 14 is directly treated under heating in an acidic solvent system, such as concentrated HCl—AcOH (hydrochloric acid-acetic acid), concentrated HCl-dioxane (hydrochloric acid-dioxane), HCl-MeOH (hydrochloric acid-methanol), 6M $H_2SO_4$-dioxane (sulfuric acid-dioxane), and concentrated $H_2SO_4$-dioxane, to afford a crude compound of formula 11 or 15. The crude compound of formula 11 or 15, without further purification, is converted to carprofen in the same manner as stated in Scheme 2.

One feature of the invention, as depicted in Schemes 1-3, is the use of cyclohexanone as a starting material. Cyclohexanone is readily available at a reasonable price. Sigma-Aldrich sells it at $105.00 per 2 liters. Larger quantity of cyclohexanone can be purchased at a cheaper unit price.

Another feature of the invention is that the processes are designed such that purification of most of the intermediates, before using them in the subsequent reactions, is optional. As a result, consecutive reaction steps may be carried out, one after another, without purification of the intermediates formed therein, which greatly simplifies the processes and leads to higher yields. Such reaction steps may even be carried out in one reaction container—making them one-pot reactions.

By the term "purification", it means that utilizing conventional purification methods, such as crystallization or running a flash column chromatography, to obtain a compound with a reasonable degree of purity. One skilled in the art would understand that the conventional purification methods are time consuming and often cause loss of yield in exchange of higher purity. Nevertheless, purification of an intermediate is often necessary because impurities contained in the intermediate often interfere with a subsequent reaction of the intermediate (either making the subsequent reaction unworkable or having a low yield). Well-designed reaction schemes, as disclosed in the present application, advantageously avoid the need to purify multiple intermediates, thereby leading to efficient processes with high yields.

As elaborated above, the crude enamine of formula 3, the crude compound of formula 12, and the crude compound of formula 14 in Scheme 3 may all be obtained by a simple work up procedure (e.g., extraction, washing, filtration, or evaporation of the reaction mixture), and then used directly in the next reaction steps, respectively. Likewise, the crude enamine of formula 3, the crude compound of formula 10, and other compounds in Scheme 1 may also be used directly, without purification, in the next reaction steps, respectively. It should be noted that the work up procedure is not considered purification because a crude product after the work up procedure still contains organic impurities, and maybe some inorganic impurities as well.

The processes of the present invention are also suitable for preparing carprofen derivatives. For instance, the diazonium salt compounds used in the above processes are derived from substituted phenyl amines. Depending on the types of carprofen derivatives to be prepared, one may simply choose different substituted phenyl amines to prepare diazonium salt. In some embodiments, the substituted phenyl amines may be aniline, 4-chloroaninline, 4-bromoaniline, or 3-chloroaniline. As another example, one may use different α-substituted carboxylic acid ester to react with an enamine in order to arrive at different carprofen analogs. As yet another example, the types of enamine can also vary by starting with different ketone as starting materials.

FIG. 3 shows some variations of the reagents used in the processes. X may by chloride or bromide; and the base may be sodium hydride, $NaOR_1$, DIEA, triethylamine, or DBU; and $R_1$ may be hydrogen, methyl, ethyl, or $C_3$-$C_6$ alkyl group.

In another aspect, the present invention provides chemicals, intermediates, and their derivatives that are prepared by the above processes. The chemicals, intermediates, and their derivatives may be usable in preparing carprofen and its derivatives. Such chemicals or intermediates include, without limitation, formulae with the following structures:

Compounds of formula 10':

$R_1$ = H, Me, Et, C3-C6 alkyl
$R_2$ = H, 4-Cl, 3-Cl, 2-Cl, 4-Br, 4-F, 3,4-Di-$Cl_2$, etc
$R_3$ = H, Me, Et, C3-C6 alkyl
N = 0, 1, 2, 3,......

when $R_2$=4-Cl, $R_3$=Me, n=1, the above structure represents the compound of formula 10.

Compounds of formula 11':

R$_1$ = H, Me, Et, C3-C6 alkyl
R$_2$ = H, 4-Cl, 3-Cl, 2-Cl, 4-Br, 4-F, 3,4-Di-Cl$_2$, etc
R$_3$ = H, Me, Et, C3-C6 alkyl
N = 0, 1, 2, 3, ......

when R$_2$=4-Cl, R$_3$=Me, n=1, the above structure represents the compound of formula 11.

Compounds of formula 14':

R$_1$ = H, Me, Et, C3-C6 alkyl
R$_2$ = H, 4-Cl, 3-Cl, 2-Cl, 4-Br, 4-F, 3,4-Di-Cl$_2$, etc
R$_3$ = H, Me, Et, C3-C6 alkyl
N = 0, 1, 2, 3, ......

when R$_2$=4-Cl, R$_3$=Me, n=1, the above structure represents the compound of formula 14.

Compounds of formula 15':

R$_1$ = H, Me, Et, C3-C6 alkyl
R$_2$ = H, 4-Cl, 3-Cl, 2-Cl, 4-Br, 4-F, 3,4-Di-Cl$_2$, etc
R$_3$ = H, Me, Et, C3-C6 alkyl
N = 0, 1, 2, 3, ......

when R$_2$=4-Cl, R$_3$=Me, n=1, the above structure represents the compound of formula 15.

EXAMPLES

Example 1

1-(cyclohex-1-en-1-yl)pyrrolidine

To a 10 L reactor equipped with condenser and Dean-stark head was added cyclohexanone (1449 g), pyrrolidine (1 kg), macroporous sulfonic acid resin (50 g) and toluene (1.5 L). The reaction mixture was heated to reflux and monitored by GC. After 7 h reflux, GC showed reaction complete. Toluene was then removed by evaporation and the residue was distilled under vacuum to afford 1-(cyclohex-1-en-1-yl)pyrrolidine, 1673 g (78.6%). $^1$HNMR (CDCl$_3$): δ 4.26 (s, 1H), 2.97 (s, 4H), 2.16 (s, 2H), 2.07 (s, 2H), 1.80 (s, 4H), 1.66 (m, 2H), 1.53 (m, 2H).

Example 2

Methyl 2-(2-oxocyclohexyl)propanoate

To 1 1 L round bottom flask containing 1-(cyclohex-1-en-1-yl)pyrrolidine (50 g) and methanol (500 mL) was added ethyl 2-bromopropanoate (60 g). The mixture was heated to reflux while stirring for 29 hours. To the reaction mixture was then added water (60 mL). Reflux was continued for another hour. The mixture was then cooled to room temperature followed by dilution with water (500 mL). The resulted mixture was extracted with t-butyl methyl ether (MTBE) (2×300 mL). The organic extracts were combined, washed with brine, dried over sodium sulfate and filtered. The filtrate was concentrated. The crude product was distilled under vacuum to give pure product, 7 g (11.5%). $^1$HNMR (CDCl$_3$): δ 3.66 (d, 3H), 2.71-2.59 (mm, 2H), 2.32 (m, 2H), 2.03 (m, 2H), 1.86 (m, 1H), 1.62 (m, 2H), 1.32 (m, 1H), 1.12-1.05 (dd, 3H). MS (ESI) m/z 185.2 [M+1]$^+$.

Example 3 methyl 2-(3-formyl-2-oxocyclohexyl)propanoate

To a 250 mL round bottom flask under nitrogen was charged with sodium hydride (2.2 g, 60% in mineral oil) followed by dropwise addition of THF (50 mL) while stirring at room temperature. A solution of methyl 2-(2-oxocyclohexyl)propanoate (5 g), formic acid methyl ester (1.6 g), and anhydrous methanol (0.1 mL) in THF (10 mL) was then added slowly to the mixture in such speed so that the internal temperature is controlled below 25° C. After the addition, the reaction mixture was stirred at room temperature for another 5 hours, followed by treatment with water (100 mL). The resulted mixture was extracted with methyl t-butyl ether (MTBE) twice (2×50 mL). The organic extracts were combined, washed with brine, dried over sodium sulfate, filtered and concentrated. The crude product was then purified by column chromatography (petroleum ether:ethyl acetate=10:1) to give 1 g (17%) pure product. $^1$HNMR (CDCl$_3$): δ 8.26 (dd, 1H), 3.65 (d, 3H), 3.10 (m, 1H), 2.90-2.75 (mm, 1H), 2.26 (m, 2H), 1.86 (m, 2H), 1.72 (m, 1H), 1.47 (m, 2H), 1.18-1.05 (dd, 3H). MS (ESI) m/z 213.1 [M+1]$^+$.

Example 4

(E)-methyl 2-(3-(2-(4-chlorophenyl)hydrazono)-2-oxocyclohexyl)propanoate

To a 100 mL flask was charged hydrochloric acid (6N, 1.5 mL) and 4-chloroaniline (0.9 g). The mixture was stirred at room temperature until a clear solution formed followed by cooling in ice-water bath to internal temperature at ~0° C. A solution of sodium nitrite (0.5 g) in water (3 mL) was then added dropwise. The mixture was stirred for another 30 min at 0° C. after the completion of the addition.

In another flask containing a solution of methyl 2-(3-formyl-2-oxocyclohexyl)propanoate (1.3 g) in methanol (7 mL) was treated with a solution sodium acetate (1.3 g) in water (6 mL) while stirring. This mixture was then cooled to 0° C., followed by slow addition of above 4-chlorophenyl diazonium chloride mixture. The mixture was then stirred at 0° C. for another two and a half hours. The resulted mixture was then treated with water. The water layer was then removed and the oily semi-solid was used directly for next step without further purification. MS (ESI) m/z 323.1 [M+1]$^+$.

Example 5

2-(6-chloro-1-oxo-2,3,4,9-tetrahydro-1H-carbazol-2-yl)propanoic acid

A mixture of crude product from Example 4, acetic acid (10 mL), and concentrated hydrochloric acid (2 mL) was heated to reflux for 1 hour. The reaction mixture was then poured into ice-water (50 mL) while stirring. The yellow solid was collected by filtration. The yellow solid product was then treated with acetone (2 mL) with stirring until the mixture became a uniform suspension. The solid suspension was then collected by filtration and washing with minimum cold acetone twice to give a solid product, 0.4 g (22.4% from (E)-methyl 2-(3-(2-(4-chlorophenyl)hydrazono)-2-oxocyclohexyl)propanoate). $^1$HNMR (DMSO-d$_6$): δ 12.18 (s, 1H), 11.73 (s, 1H), 7.72 (d, 1H), 7.37 (d, 1H), 7.26 (d, 1H), 3.04 (m, 3H), 2.86 (m, 1H), 2.10 (m, 1H), 2.00 (m, 1H), 1.01 (d, 3H). MS (ESI) m/z 292.1 [M+1]$^+$.

Example 6

Carprofen from 2-(6-chloro-1-oxo-2,3,4,9-tetrahydro-1H-carbazol-2-yl)propanoic acid A mixture of 2-(6-chloro-1-oxo-2,3,4,9-tetrahydro-1H-carbazol-2-yl)propanoic acid (0.38 g, example 5) and pyridinium hydrochloride (0.36 g) was heated to 230° C. under nitrogen for 3 hours. The mixture was then treated with ice water while still hot followed by stirring for 20 minutes at room temperature. The resulted mixture was extracted with methyl t-butyl ether (MTBE) twice (2×50 mL). The combined MTBE extracts was dried over sodium sulfate, filtered, and evaporated to give title product. $^1$HNMR (DMSO-d$_6$): δ 12.26 (s, 1H), 11.32 (s, 1H), 8.14 (d, 1H), 8.05 (d, 1H), 7.45 (d, 1H), 7.37 (s, 1H), 7.32 (d, 1H), 7.07 (d, 1H), 3.79 (t, 1H), 1.40 (d, 3H). MS (ESI) m/z 274.1 [M+1]$^+$.

Example 7 methyl 2-(2-(pyrrolidin-1-yl)cyclohex-2-en-1-yl)propanoate

To a 1 L round bottom flask was added 1-(cyclohex-1-en-1-yl)pyrrolidine (100 g, example 1), acetonitrile (800 mL), methyl 2-bromopropanoate (116.3 g), and sodium iodide (9.9 g). The mixture was then heated to reflux while stirring for 20 hours. The mixture was cooled to room temperature, added DBU (100.3 g), and stirred for 30 minutes. The resulted mixture was then concentrated to remove most acetonitrile, followed by addition of toluene (500 mL). The suspension was stirred at room temperature for 1 hour followed by filtration. The filter cake was washed with small amount of toluene twice. The combined toluene solution was distilled under vacuum to give a liquid product, 143.4 g (91.4%). $^1$HNMR (CDCl$_3$): δ 4.64 (t, 1H), 3.60 (s, 3H), 2.99 (q, 2H), 2.73 (m, 2H), 2.56 (m, 2H), 2.05 (m, 1H), 1.97 (m, 1H), 1.73 (m, 5H), 1.54 (m, 3H), 1.01 (d, 3H).

Example 7

4-chlorophenyldiazonium tetrafluoroborate

To a 250 mL round bottom flask was added tetrafluoroboric acid solution (34 mL, 50%) and water (40 mL). The mixture was stirred and cooled to ~10° C. with cold water bath, followed by addition of 4-chloroanaline (12.7 g). The mixture was stirred at the same temperature until clear solution was formed. The resulted solution was then cooled in ice-water bath to ~0° C. A solution of sodium nitrite (6.9 g) in water (15 mL) was added dropwise in such speed that the internal temperature below 10° C. After the addition, the mixture was stirred in ice-water bath for another 30 minutes. The white solid was collected by filtration. The crude solid product was dissolved in acetone (50 mL) followed by treatment of cold ethyl ether (100 mL). The solid was collected again by filtration and washed with cold acetone twice (2×50 mL) to give white pure solid product, 19 g (84.1%). $^1$HNMR (DMSO-d$_6$): δ 8.62 (d, 2H), 8.04 (d, 2H). MS (ESI) m/z 139.0 [M+1]$^+$.

Example 8

(E)-1-(2-(2-(4-chlorophenyl)hydrazono)-6-(1-methoxy-1-oxopropan-2-yl)cyclohexylidene)pyrrolidin-1-ium tetrafluoroborate A solution of methyl 2-(2-(pyrrolidin-1-yl)cyclohex-2-en-1-yl)propanoate (5 g, example 7) in methylene chloride (165 mL) was cooled in dry ice-acetone bath to ~−78° C., followed by portionwise addition of 4-chlorophenyldiazonium tetrafluoroborate (4.8 g) while stirring. After the addition, the mixture was warmed to room temperature in 2 hours by removing the dry ice-acetone bath. The mixture was the treated with dilute hydrochloric acid (1M, 100 mL) with stirring. The resulted solution was extracted with methylene chloride twice (2×100 mL). The combined methylene chloride phase was concentrated to give crude oily product. The crude product was purified by column chromatography using petroleum ether—ethyl acetate as eluent with ratio of 4:1, 1:1, 1:2, and pure ethyl acetate to sequentially elute the silico gel column to give pure product, 2.2 g (22.6%). $^1$HNMR (CDCl$_3$): δ 9.44 (s, 1H), 7.21 (s, 4H), 4.24 (m, 2H), 4.12 (m, 2H), 3.62 (s, 3H), 3.32 (m, 1H), 2.81 (m, 2H), 2.64 (m, 1H), 2.11 (m, 6H), 1.80 (m, 2H), 1.15 (d, 3H). MS (ESI) m/z 376.2 [M]$^+$.

Example 9

1-(6-chloro-2-(1-methoxy-1-oxopropan-2-yl)-2,3,4,9-tetrahydro-1H-carbazol-1-ylidene)pyrrolidin-1-ium tetrafluoroborate To a 500 mL three-neck round bottom flask equipped with thermometer, mechanic stirrer, and Dean-Stark head with cooling condenser was charged with polyphosphoric acid (PPA, 300 mL). The PPA was then heated to 120° C. while stirring. A solution of (E)-1-(2-(2-(4-chlorophenyl)hydrazono)-6-(1-methoxy-1-oxopropan-2-yl)cyclohexylidene)pyrrolidin-1-iumtetrafluoroborate (34.6 g) in methylene chloride (100 mL) was added slowly. Methylene chloride was evaporated during the addition and collected through Dean-Stark head with cooling condenser. After the addition, heating was continued at ~120° C. for 3 hours. The hot liquid mixture was treated with hot water (800 mL) to form a solution. The resulted solution was then extracted with methylene chloride (5×300 mL). The combined organic phase was washed with water (500 mL), dried over sodium sulfate, filtered and evaporated to afford 9 g (27.1%) crude product which was purified by column chromatography (elution with sequentially with petroleum ether/ethyl acetate (1:1) then ethyl acetate) to give pure product. $^1$HNMR (CDCl$_3$): δ 10.20 (s, 1H), 7.56 (dd, 1H), 7.43 (d, 1H), 7.30 (d, 1H), 4.60 (m, 1H), 4.40 (m, 1H), 4.20 (m, 1H), 4.15 (m, 1H), 4.00 (m, 1H), 3.69-3.61 (d, 3H), 3.05 (m, 1H), 2.73 (m, 2H), 2.40 (m, 2H), 2.16 (m, 4H), 1.36-1.22 (dd, 3H). MS (ESI) m/z 359.1 [M]$^+$.

Example 10

Carprofen from 1-(6-chloro-2-(1-methoxy-1-oxo-propan-2-yl)-2,3,4,9-tetrahydro-1H-carbazol-1-ylidene)pyrrolidin-1-ium tetrafluoroborate (Example 9)

A mixture of 1-(6-chloro-2-(1-methoxy-1-oxopropan-2-yl)-2,3,4,9-tetrahydro-1H-carbazol-1-ylidene)pyrrolidin-1-ium tetrafluoroborate (1 g, example 9) and pyridinium hydrochloride was heated to 200° C. under nitrogen for 1 hour. The mixture was dissolved in methanol (50 mL) while hot followed by treatment with water (50 mL). Solid was collected by filtration to afford crude product. The crude product was dissolved in ethyl acetate (100 mL) followed by washing with water (100 mL). Insoluble suspension was removed by filtration. Organic phase was then separated, washed with brine, dried over sodium sulfate and evaporated to give title compound, 0.5 g (81.8%). MS (ESI) m/z 274.10 [M]$^+$.

Example 11

Carprofen Directly from 1-(cyclohex-1-en-1-yl)pyrrolidine (Example 1) without Purification of Intermediates To a 250 mL reactor was added 1-(cyclohex-1-en-1-yl)pyrrolidine (50 g, example 1), methyl 2-bromopropanoate (55.2 g), 2.5 g sodium iodide and 100 mL acetonitrile. The mixture was then heated to reflux for 16.5 hours, then cooled to 0° C. in ice-water bath. 19.6 g Sodium methoxide was then added portionwise so that internal temperature was kept below 5° C. After the addition, stirring was continued at 0° C. for 1 hour followed by rotary evaporation to remove all acetonitrile. 120 mL toluene was then added to the residue and the resulted mixture was stirred at room temperature for 20 min. The solid was then removed by filtration and washed twice with 2×15 mL toluene. The toluene filtrate and washings were combined and evaporated to remove all toluene to afford 80 g crude product, methyl 2-(2-(pyrrolidin-1-yl)cyclohex-2-en-1-yl)propanoate, which was used directly for next step.

To a 500 mL reactor was added above crude intermediate (80 g) and 160 mL THF. The solution was cooled to 0° C. while stirring followed by portion wise addition of 4-chlorophenyldiazonium tetrafluoroborate (45.8 g, example 7) in such speed so that internal temperature was <5° C. The mixture was stirred at 0° C. for 1 hour after the addition, then stirred at room temperature for 1 hour. The reaction mixture was evaporated to remove all THF to give a deeply colored and oily product, (E)-1-(2-(2-(4-chlorophenyl)hydrazono)-6-(1-methoxy-1-oxopropan-2-yl)cyclohexylidene)pyrrolidin-1-iumtetrafluoroborate, which was used directly for next step.

To above reactor containing (E)-1-(2-(2-(4-chlorophenyl)hydrazono)-6-(1-methoxy-1-oxopropan-2-yl)cyclohexylidene)pyrrolidin-1-iumtetrafluoroborate was charged with 224 mL methanol and 56 mL concentrated hydrochloric acid. The mixture was heated to reflux for 12 hour. The reaction mixture was then cooled to room temperature then stirred for 30 min. The solid was collected by filtration and washed with 3×15 mL ethanol twice to get an whitish solid product, methyl 2-(6-chloro-1-oxo-2,3,4,9-tetrahydro-1H-carbazol-2-yl)propanoate, 15.2 g (15.0% from 1-(cyclohex-1-en-1-yl)pyrrolidine). $^1$HNMR (DMSO-d$_6$): δ 11.75 (s, 1H), 7.72 (s, 1H), 7.37 (d, 1H), 7.28 (d, 1H), 7.61 (s, 3H), 3.04 (m, 3H), 2.86 (m, 1H), 2.12 (m, 1H), 2.01 (m, 1H), 1.05 (d, 3H). MS (ESI) m/z 306.1 [M]$^+$.

To a 100 mL reactor was charged with above methyl 2-(6-chloro-1-oxo-2,3,4,9-tetrahydro-1H-carbazol-2-yl)propanoate (10 g) and pyridinium hydrochloride (11.4 g), the flask is flashed with nitrogen to remove oxygen from the flask, and then heated to 200° C. for 3 hours. The mixture was poured into 100 mL ice water while still hot. The reactor was rinsed with 30 mL methanol and the methanol solution was poured into the ice water mixture too. The mixture was then stirred at room temperature for 30 min. The solid was collected by filtration and washed twice with water (2×30 mL) and oven dried under vacuum and heating.

The above crude carprofen (9.5 g) was stirred at room temperature with 50 mL acetone to make a clear solution, followed by dropwise addition of trimethylamine (7 g, 2 eq). Stirring was continued after the addition for 1 hour. Solid was collected by filtration and dried under heating to give 9.4 g carprofenate trimethylamine salt.

A mixture of the above 9.4 g salt in 100 mL water was heated to 60° C. while stirring. The mixture is still a suspension after 10 min heating at 60° C. while stirring. 15 mL 5% HCl was added to this suspension to make a pH=3. Stirring at 60° C. was continued for 20 min and then room temperature for 1 hour. The solid was collected by filtration, washed with water twice (2×15 mL) and dried in oven under vacuum and heating at 60° C. to give title product, carprofen, 7.4 g (82.7%). $^1$HNMR (DMSO-d$_6$): δ 12.26 (s, 1H), 11.32 (s, 1H), 8.14 (d, 1H), 8.05 (d, 1H), 7.45 (d, 1H), 7.37 (s, 1H), 7.32 (d, 1H), 7.07 (d, 1H), 3.79 (t, 1H), 1.40 (d, 3H). MS (ESI) m/z 274.1 [M+1]$^+$.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A process for preparing carprofen comprising the steps of:
   (1) reacting an enamine of formula 3 with an α-substituted carboxylic acid ester of formula 4 in a first organic solvent followed by treatment with a base to afford an enamine of formula 12;

3

4

-continued

12

R₁ is Me, Et, C₃-C₆ alkyl (2) reacting the enamine of formula 12 in a second organic solvent with an aqueous solution of a substituted phenyldiazonium salt of formula 9' to give a compound of formula 14";

9'

14"

Y⁻ is chloride or tetrafluoroboric anion
R₁ is H, Me, Et, C₃-C₆ alkyl;
Y⁻ is chloride or tetrafluoroboric anion

(3) heating a mixture of the compound of formula 14" in a third organic solvent system to form a compound of formula 11;

11

R₁ is Me, Et, C₃-C₆ alkyl or, heating a mixture of formula 14" in a fourth organic solvent system to form a compound of formula 15"; and

15"

R₁ is H, Me, Et, C₃-C₆ alkyl;
Y⁻ is chloride or tetrafluoroboric anion (4) heating a mixture of the compound of formula 11 or 15" in the presence of an organic salt to yield carprofen.

2. The process of claim 1, wherein a crude compound of any of formula 3, 11, 12, 14", and 15", without being purified by crystallization or flash column chromatography, is directly used in the process.

3. The process of claim 1, wherein the base is diisopropylethylamine, 1,8-diazabicyclo[5.4.0]undec-7-ene, sodium alkoxide, potassium carbonate, cesium carbonate, sodium hydride, sodium alkoxide, potassium carbonate, or cesium carbonate.

4. The process of claim 1, wherein the step (1) further comprises using sodium iodide as a catalyst in the reaction prior to the base treatment.

5. The process of claim 1, wherein the substituted phenyldiazonium salt of formula 9' is prepared from an aniline compound by treating it with sodium nitrite and tetrafluoroboric acid in an aqueous medium.

6. The process of claim 5, wherein the aniline compound is aniline, 4-chloroaninline, 4-bromoaniline, or 3-chloroaniline.

7. The process of claim 1, wherein the step (3) further comprises using acidic catalyst, wherein the acidic catalyst is polyphosphoric acid, 7.7 wt. % phosphorus pentoxide in methanesulfonic acid, or concentrated sulfuric acid in dioxane.

8. The process of claim 1, wherein the organic salt is pyridine hydrochloride.

* * * * *